US 011475988B1

(12) United States Patent
Burkart et al.

(10) Patent No.: US 11,475,988 B1
(45) Date of Patent: Oct. 18, 2022

(54) IMPUTATION OF BLOOD GLUCOSE MONITORING DATA

(71) Applicant: Verily Life Sciences LLC, Mountain View, CA (US)

(72) Inventors: Joshua Burkart, Boston, MA (US); Nathan Dickerson Beach, Somerville, MA (US)

(73) Assignee: Verily Ufe Sciences LLC, Mountain View, CA (US)

(*) Notice: Subject to any disclaimer, the term of this patent is extended or adjusted under 35 U.S.C. 154(b) by 859 days.

(21) Appl. No.: 16/249,633

(22) Filed: Jan. 16, 2019

Related U.S. Application Data

(60) Provisional application No. 62/618,474, filed on Jan. 17, 2018.

(51) Int. Cl.
G16H 20/60 (2018.01)
G16H 40/63 (2018.01)

(52) U.S. Cl.
CPC ............. *G16H 20/60* (2018.01); *G16H 40/63* (2018.01)

(58) Field of Classification Search
CPC ................................ G16H 20/60; G16H 40/63
See application file for complete search history.

(56) References Cited

U.S. PATENT DOCUMENTS

| | | | |
|---|---|---|---|
| 6,553,386 B1 | 4/2003 | Alabaster | |
| 8,249,946 B2 | 8/2012 | Froseth et al. | |
| 8,597,570 B2 | 12/2013 | Terashima et al. | |
| 2002/0032583 A1 | 3/2002 | Joao | |
| 2008/0201169 A1 | 8/2008 | Galasso et al. | |
| 2008/0208027 A1 | 8/2008 | Heaton | |
| 2009/0177068 A1* | 7/2009 | Stivoric | A61B 5/0022 600/365 |
| 2013/0325504 A1 | 12/2013 | Greene et al. | |
| 2014/0128705 A1* | 5/2014 | Mazlish | A61B 5/743 600/365 |
| 2015/0045641 A1 | 2/2015 | Rule | |
| 2015/0141770 A1 | 5/2015 | Rastogi et al. | |
| 2015/0289823 A1 | 10/2015 | Rack-Gomer et al. | |
| 2016/0378937 A1 | 12/2016 | Soni et al. | |

(Continued)

OTHER PUBLICATIONS

Albers, David J. et al., "Personalized glucose forecasting for type 2 diabetes using data assimilation;" PLoS Comput Biol 13(4): e1005232. https://doi.org/10.1371/journal.pcbi.1005232; Apr. 27, 2017; pp. 1-38.

(Continued)

*Primary Examiner* — Michael Tomaszewski
(74) *Attorney, Agent, or Firm* — Perkins Coie LLP

(57) ABSTRACT

Introduced here are diabetes management platforms able to impute blood glucose level values for a subject whose glycemic health state is being monitored. These imputed values can be used to estimate the glycemic health state of the subject at a given point in time, identify appropriate recommendations for improving the glycemic health state, etc. More specifically, a diabetes management platform can initially acquire one or more explicit data values generated by a glucose monitoring device. The diabetes management platform can then design a statistical model for imputing data values based on the one or more explicit data values. The diabetes management platform may employ several different computational techniques for performing imputation.

19 Claims, 12 Drawing Sheets

(56) References Cited

U.S. PATENT DOCUMENTS

2017/0128007 A1  5/2017  Hayter et al.
2017/0220751 A1  8/2017  Davis et al.
2018/0197628 A1  7/2018  Wei et al.
2019/0290172 A1  9/2019  Hadad et al.

OTHER PUBLICATIONS

Lim, Teck-Onn et al., "Bimodality in Blood Glucose Distribution; Is it universal?"; Clinical Research Centre, the Department of Nephrology, and the Public Health Institute, Kuala Lumpur, Malaysia; Apr. 10, 2002; pp. 2212-2217.
Vittinghoff, Eric et al., Regression Methods in Biostatistics: Linear, Logistic, Survival, and Repeated Measures Models; ISBN 0-387-20275-7; San Francisco, CA; Oct. 2004; 346 pages.

* cited by examiner

600

601

Acquire explicit data values representing static measurements of blood glucose level

602

Examine the explicit data values to identify a feature indicative of a glycemic characteristic of a subject

603

Design a statistical model based on the explicit data values, corresponding time points, and/or glycemic characteristic

604

Apply the statistical model to the explicit data values to impute data values

605

Construct data series from the explicit data values and/or the imputed data values

606

Store the data series in a database record associated with a subject profile

FIGURE 6

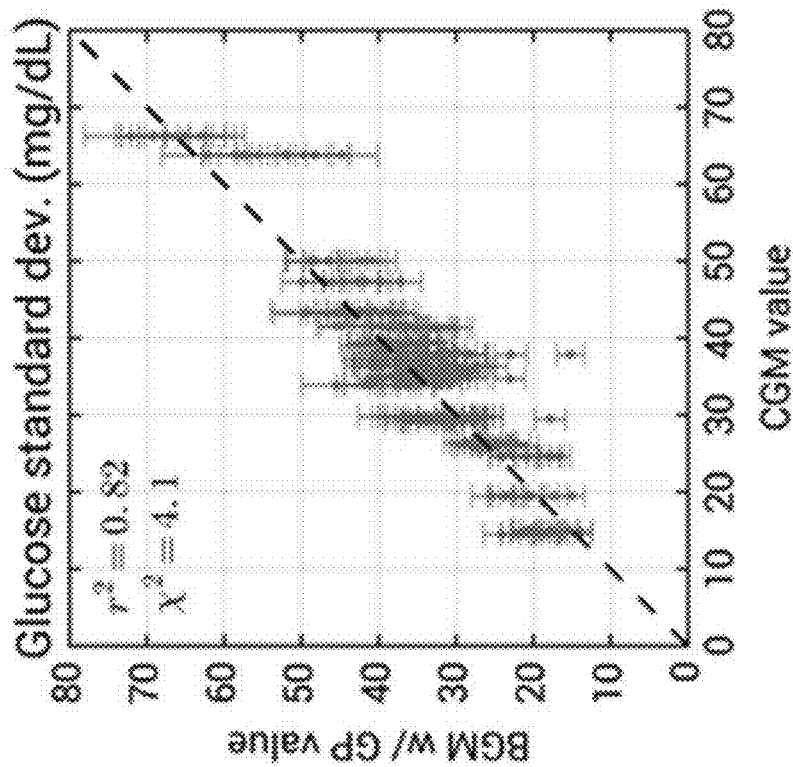
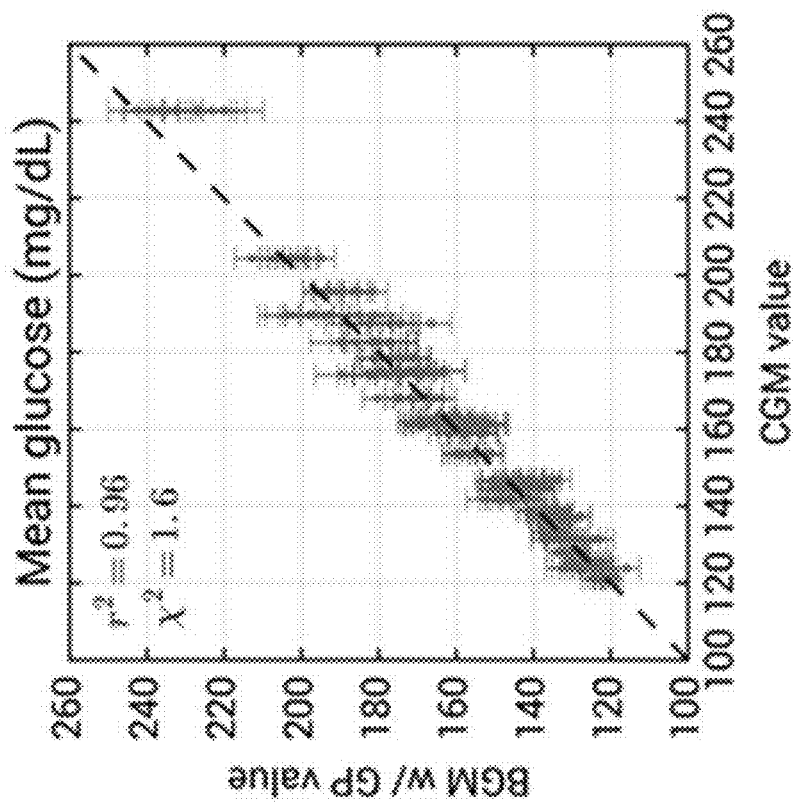
FIGURE 9

IMPUTATION OF BLOOD GLUCOSE MONITORING DATA

CROSS-REFERENCE TO RELATED APPLICATIONS

This application claims priority to U.S. Provisional Application No. 62/618,474, titled "Imputation of Blood Glucose Monitoring Data" and filed on Jan. 17, 2018, which is incorporated by reference herein in its entirety.

TECHNICAL FIELD

Various embodiments concern computer programs and associated computer-implemented techniques for imputing glucose measurements to estimate glycemic health state at a given point in time.

BACKGROUND

After ingestion of a foodstuff that contains carbohydrates, the human body breaks down the carbohydrates into glucose, which serves as a source of energy for the cells of the human body. Glucose is transported via circulation within the blood stream. Therefore, ingestion of foodstuffs will influence the concentration of glucose within the blood stream (also referred to as the "blood glucose level" or "glucose level").

According to the American Diabetes Association (ADA), a normal blood glucose level for people without diabetes is below 6.9 mmol/L (125 mg/dL). Meanwhile, the target blood glucose range for people with diabetes is 5.0-7.2 mmol/L (90-130 mg/dL) before meals and less than 10 mmol/L (180 mg/dL) after meals. However, some people with diabetes struggle to consistently stay within the recommended range.

BRIEF DESCRIPTION OF THE DRAWINGS

Various features and characteristics of the technology will become more apparent to those skilled in the art from a study of the Detailed Description in conjunction with the drawings. Embodiments of the technology are illustrated by way of example and not limitation in the drawings, in which like references may indicate similar elements.

FIG. 6 depicts a flow diagram of a process for producing a statistical model for probabilistically imputing data values where explicit data values have not been generated.

FIG. 9 is an alternate visualization for when the number of measurements per day is seven.

Figure 1:
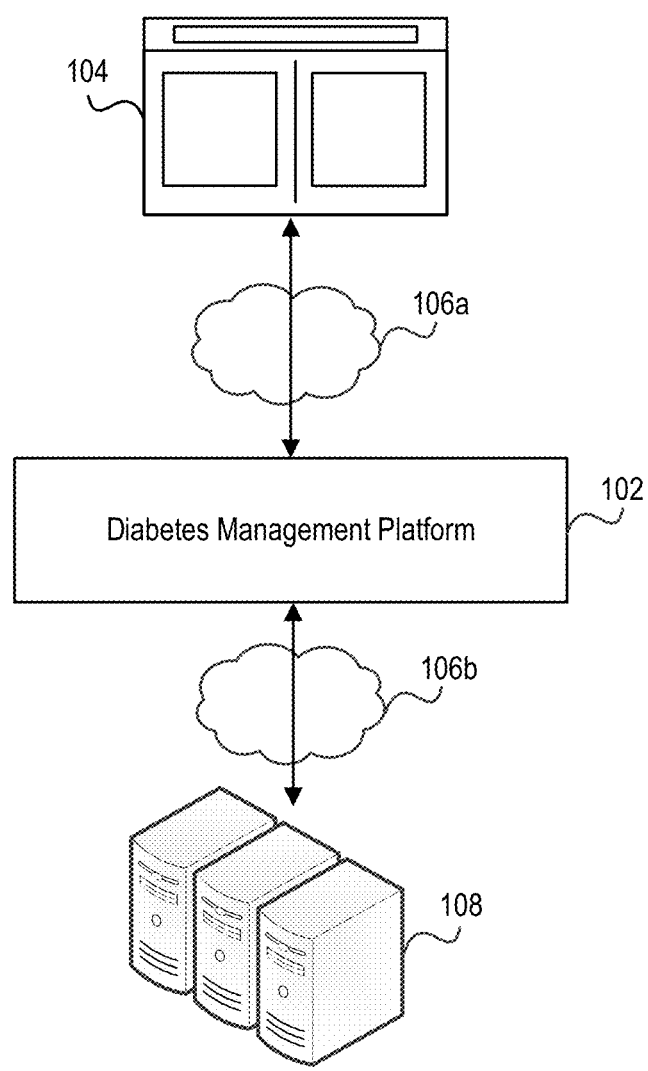
FIG. 1 illustrates a network environment that includes a diabetes management platform.

The drawings depict various embodiments for the purpose of illustration only. Those skilled in the art will recognize that alternative embodiments may be employed without departing from the principles of the technology. Accordingly, while specific embodiments are shown in the drawings, the technology is amenable to various modifications.

DETAILED DESCRIPTION

Diabetes mellitus (commonly referred to as "diabetes") is a group of metabolic disorders in which the affected individuals experience high blood glucose levels over a prolonged period. If left untreated, diabetes can cause many complications. For example, long-term complications can include cardiovascular disease, stroke, chronic kidney disease, foot ulcers, and eye damage.

Individuals with diabetes can benefit from education about treatment, good nutrition to achieve a normal body weight, and exercise. However, some of those individuals may find it difficult to implement lifestyle changes that promote healthier blood glucose levels. Moreover, some of these individuals may find it difficult to understand blood glucose level measurements, which represent a technical signal indicative of the diabetes disease state.

Blood glucose monitoring is the process through which the concentration of glucose within the blood stream (also referred to as the "blood glucose level" or "glucose level") is tested. A test is typically performed by piercing the skin to draw blood, and then applying the blood to a disposable, chemically active test strip. Historically, an individual with diabetes would take several measurements throughout the day in an ad hoc manner using a blood glucose meter. Because blood glucose meters require individuals manually perform each test, measurements are often generated sporadically. However, it can be difficult to establish the blood glucose level between these discrete measurements. Moreover, it can be difficult to predict the blood glucose level at future points in time based on these discrete measurements.

Introduced here, therefore, are computer programs and associated computer-implemented techniques for imputing blood glucose level values for a subject whose glycemic health state is being monitored. These imputed values can be used to estimate the glycemic health state of the subject at a given point in time, identify appropriate recommendations for improving the glycemic health state, etc.

A diabetes management platform can initially acquire one or more explicit data values (also referred to as "explicit measurements") generated by a glucose monitoring device. Generally, the glucose monitoring device is a blood glucose monitor that monitors the blood glucose level of the subject on an ad hoc basis. An explicit data value, therefore, may represent a discrete, digitally-represented value indicative of the blood glucose concentration at a corresponding time. However, the glucose monitoring device could be a continuous glucose monitor that continually monitors the blood glucose level of the subject. Thus, an explicit data value could also represent a discrete, digitally-represented value indicative of the blood glucose concentration as sampled periodically. In such instances, the explicit data value may be one of a series of data values in a temporal order. The series of data values may be generated over the course of a natural cycle of a person or a mammalian body, such as a circadian cycle, a menstrual cycle, a feeding cycle, an elimination cycle, etc. By examining a series of data values corresponding to a natural cycle, the diabetes management platform can better understand the pattern of the blood glucose level over time. For example, a series of data values over an entire circadian cycle may be more readily interpreted than a series of data values over a portion of a circadian cycle (in which case the diabetes management platform may be unsure of which portion of the circadian cycle has been monitored)

The diabetes management platform can then impute one or more data values based on the explicit measurement(s). These imputed data values (also referred to as "imputed measurements") can be used to personalize a testing/treatment regimen. The diabetes management platform may employ several different computational techniques for performing imputation.

One example of such a computational technique is a Gaussian process. A Gaussian process may be preferred over other computation techniques because causes finite collections of random variables to have a multivariate normal distribution, which may account for the actual biological processes of the human body. For a Gaussian process, the diabetes management platform can use a radial basis kernel designed to capture a correlation timescale and a periodic kernel designed to capture typical periodic patterns (e.g., daily, weekly, or monthly patterns). More specifically, the radial basis kernel can be designed to indicate that the blood glucose level is less likely to change over short timeframes (e.g., several seconds) than long timeframes (e.g., several hours), while the periodic kernel can be designed to ensure that imputed data values conform with a periodic pattern of past explicit data values.

Another example of such a computational technique is Kalman filtering (also referred to as "linear quadratic estimation"). For Kalman filtering, the diabetes management platform can track variance values indicative of the uncertainty of the imputed data values. By estimating a joint probability distribution over the imputed data values, the diabetes management platform can increase imputation accuracy over other techniques that are based on a single measurement. The diabetes management model can also update the imputed data values and/or the variance values using a state transition model. The state transition model can be based on ordinary differential equation(s) representing the relevant biological responses.

Thus, the diabetes management platform can perform two separate processes. First, the diabetes management platform can train/configure a statistical model for a subject. For example, the diabetes management platform can acquire explicit data values (e.g., from a blood glucose meter), identify a historical feature by parsing the explicit data values, and train and/or configure a statistical based at least in part on the historical feature. Second, the diabetes management platform can test/apply the statistical model. For example, the diabetes management platform can acquire one or more new explicit data values, identify a new feature by parsing the new explicit data value(s), and apply at least the new feature against the trained/configured statistical model.

Embodiments may be described with reference to particular computer programs, system configurations, networks, etc. However, those skilled in the art will recognize that these features are equally applicable to other computer program types, system configurations, network types, etc. Moreover, the technology can be embodied using special-purpose hardware (e.g., circuitry), programmable circuitry appropriately programmed with software and/or firmware, or a combination of special-purpose hardware and programmable circuitry. Accordingly, embodiments may include a machine-readable medium having instructions that may be used to program an electronic device to perform a process for examining explicit data values of blood glucose level, imputing data values of blood glucose level, producing visualizations of blood glucose level using explicit value(s) and/or imputed data value(s), etc.

Terminology

References in this description to "an embodiment" or "one embodiment" means that the particular feature, function, structure, or characteristic being described is included in at least one embodiment. Occurrences of such phrases do not necessarily refer to the same embodiment, nor are they necessarily referring to alternative embodiments that are mutually exclusive of one another.

Unless the context clearly requires otherwise, the words "comprise" and "comprising" are to be construed in an inclusive sense rather than an exclusive or exhaustive sense (i.e., in the sense of "including but not limited to"). The terms "connected," "coupled," or any variant thereof is intended to include any connection or coupling between two or more elements, either direct or indirect. The coupling/connection can be physical, logical, or a combination thereof. For example, devices may be electrically or communicatively coupled to one another despite not sharing a physical connection.

The term "based on" is also to be construed in an inclusive sense rather than an exclusive or exhaustive sense. Thus, unless otherwise noted, the term "based on" is intended to mean "based at least in part on."

The term "module" refers broadly to software components, hardware components, and/or firmware components. Modules are typically functional components that can generate useful data or other output(s) based on specified input(s). A module may be self-contained. A computer program may include one or more modules. Thus, a computer program may include multiple modules responsible for completing different tasks or a single module responsible for completing all tasks.

When used in reference to a list of multiple items, the word "or" is intended to cover all of the following interpretations: any of the items in the list, all of the items in the list, and any combination of items in the list.

The sequences of steps performed in any of the processes described here are exemplary. However, unless contrary to physical possibility, the steps may be performed in various sequences and combinations. For example, steps could be added to, or removed from, the processes described here. Similarly, steps could be replaced or reordered. Thus, descriptions of any processes are intended to be open-ended.

Technology Overview

FIG. 1 illustrates a network environment 100 that includes a diabetes management platform 102. Individuals can interface with the diabetes management platform 102 via an interface 104. The diabetes management platform 102 may be responsible for parsing physiological data pertaining to an individual to discover variations in the blood glucose level, impute value(s) for the blood glucose level for an upcoming time interval, generate a personalized, probabilistic model for estimating the blood glucose level, generate recommendations for guiding the individual toward a healthier glycemic health state, etc. The diabetes management platform 102 may also be responsible for creating interfaces through which the individual can view physiological data, manage preferences, etc.

Physiological data could specify the blood glucose level of the individual accessing the interface 104 or some other person. For example, in some embodiments the interface 104 enables a person with diabetes to view their own physiological data, while in other embodiments the interface 104 enables an individual to view physiological data associated with some other person. The individual may be a health coach responsible for monitoring the glycemic health of the other person. Examples of health coaches include medical professionals (e.g., a physician or nurse), diabetic health counselors, family members of the other person, etc. Some interfaces are configured to facilitate interactions between subjects and health coaches, while other interfaces are configured to serve as informative dashboards for subjects.

As noted above, the diabetes management platform 102 may reside in a network environment 100. Thus, the diabetes management platform 102 may be connected to one or more networks 106a-b. The network(s) 106a-b can include personal area networks (PANs), local area networks (LANs), wide area networks (WANs), metropolitan area networks (MANs), cellular networks, the Internet, etc. Additionally or alternatively, the diabetes management platform 102 can be communicatively coupled to computing device(s) over a short-range communication protocol, such as Bluetooth® or Near Field Communication (NFC).

The interface 104 is preferably accessible via a web browser, desktop application, mobile application, or over-the-top (OTT) application. Accordingly, the interface 104 may be viewed on a personal computer, tablet computer, personal digital assistant (PDA), mobile phone, game console, music player, wearable electronic device (e.g., a watch or fitness accessory), network-connected ("smart") electronic device, (e.g., a television or home assistant device), virtual/augmented reality system (e.g., a head-mounted display), or some other electronic device.

Some embodiments of the diabetes management platform 102 are hosted locally. That is, the diabetes management platform 102 may reside on the computing device used to access the interface 104. For example, the diabetes management platform 102 may be embodied as a mobile application executing on a mobile phone. Other embodiments of the diabetes management platform 102 are executed by a cloud computing service operated by Amazon Web Services® (AWS), Google Cloud Platform™, Microsoft Azure®, or a similar technology. In such embodiments, the diabetes management platform 102 may reside on a host computer server that is communicatively coupled to one or more content computer servers 108. The content computer server(s) 108 can include different types of data, user information (e.g., profiles, credentials, and health-related information such as age, diabetes classification, etc.), and other assets. Such information could also be stored on the host computer server.

Certain embodiments are described in the context of network-accessible interfaces. However, those skilled in the art will recognize that the interfaces need not necessarily be accessible via a network. For example, a computing device may be configured to execute a self-contained computer program that does not require network access. Instead, the self-contained computer program may cause necessary assets (e.g., physiological data, healthcare regimen data, and processing operations) to be downloaded at a single point in time or on a periodic basis (e.g., weekly, daily, or hourly).

Figure 2:
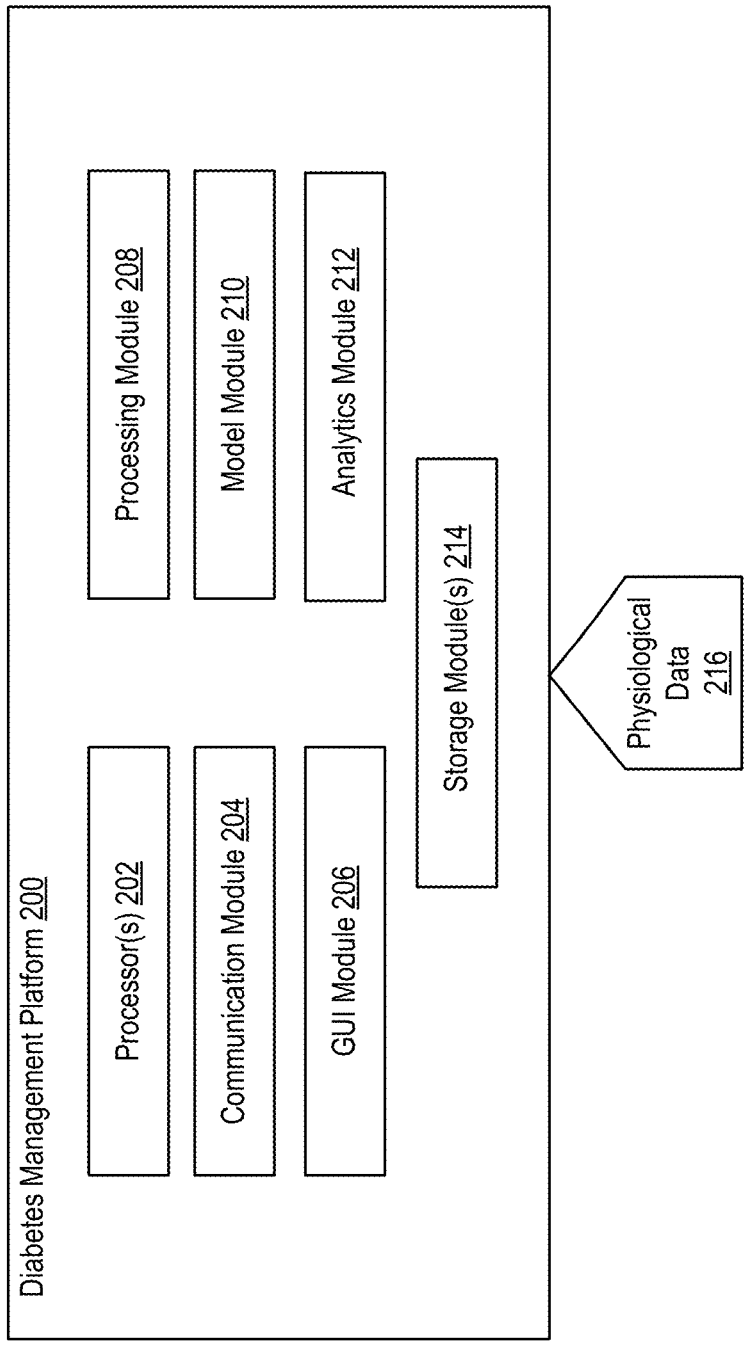
FIG. 2 depicts the high-level architecture of a diabetes management platform able to examine explicit physiological data values to enable the imputation of physiological data values.

FIG. 2 depicts the high-level architecture of a diabetes management platform 200 able to examine explicit physiological data values to enable the imputation of physiological data values. In some embodiments the imputed data values reside between explicit data values (e.g., if a subject sporadically measures the blood glucose level using a blood glucose meter), while in other embodiments the imputed data values reside in a future time interval for which there are no explicit data values. Thus, imputed data values can be applied to a personalized statistical model to generate additional data points in between explicit data values. In such embodiments, the personalized statistical model can be trained on historical explicit data values (e.g., measurements generated by a blood glucose meter).

As shown in FIG. 1, an individual can interface with the diabetes management platform 200 via an interface. The individual may be a person with diabetes or another person with an interest in the blood glucose level of the person with diabetes.

The diabetes management platform 200 can include one or more processors 202, a communication module 204, a graphical user interface (GUI) module 206, a processing module 208, a model module 210, an analytics module 212, and one or more storage modules 214. In some embodiments a single storage module includes multiple computer programs for performing different operations (e.g., format conversion and statistical analysis), while in other embodiments each computer program is hosted within a separate storage module. Embodiments of the diabetes management platform 200 may include some or all of these components, as well as other components not shown here.

The processor(s) 202 can execute modules from instructions stored in the storage module(s) 214, which can be any device or mechanism capable of storing information. For example, the processor(s) 202 may execute the GUI module 206, processing module 208, model module 210, and analytics module 212.

The communication module 204 can manage communications between various components of the diabetes management platform 200. The communication module 204 can also manage communications between the computing device on which the diabetes management platform 200 resides and another computing device.

For example, the diabetes management platform 200 may reside on a mobile phone in the form of a mobile application. In such embodiments, the communication module 204 can facilitate communication with a network-accessible computer server responsible for supporting the mobile application. The communication module 204 may facilitate communication with various data sources through the use of application programming interfaces (APIs), bulk data interfaces, etc.

As another example, the diabetes management platform 200 may reside on a server system that includes one or more network-accessible computer servers. In such embodiments, the communication module 204 can communicate with a computer program executing on the computing device associated with the individual. Those skilled in the art will recognize that the components of the diabetes management platform 200 can be distributed between the server system and the computing device associated with the individual in various manners. For example, some data (e.g., physiological data) may reside on the computing device of the individual, while other data (e.g., processing operations and modeling algorithms for imputing physiological data measurements) may reside on the server system.

The GUI module 206 can generate the interface(s) through which an individual can interact with the diabetes management platform 200. For example, an interface may include a graphical representation of the blood glucose level over time. The graphical representation may be based on explicit physiological data values, imputed physiological data values, or any combination thereof. As another example, an interface may specify a characteristic of the explicit physiological data values and/or the imputed physiological data values. These interfaces may also present feedback/suggestions for improving the glycemic health state (e.g., by performing certain activities, refraining from consuming certain foodstuffs, etc.).

The processing module 208 can apply one or more operations to physiological data 216 acquired by the diabetes management platform 200. Physiological data 216 specifying the blood glucose level of an individual could be generated by a glucose monitoring device. Examples of glucose monitoring devices include continuous glucose monitors and blood glucose meters.

A glucose monitoring device may be configured to continuously or periodically transmit physiological data 216 to the diabetes management platform 200. In some embodiments, the glucose monitoring device continually uploads physiological data 216 to the diabetes management platform 200 so long as the glucose monitoring device remains communicatively coupled to the computing device on which the diabetes management platform 200 resides (e.g., via a Bluetooth® communication channel). In other embodiments, the glucose monitoring device periodically uploads physiological data 216 to the diabetes management platform 200 on a periodic basis (e.g., hourly, daily, or weekly). In such embodiments, the physiological data 216 may include multiple data sets (e.g., a first data set for a first time interval, a second data set for a second time interval, etc.).

The processing module 208 can process the physiological data 216 into a format suitable for the other modules (e.g., the model module 210, analytics module 212, or storage module(s) 214). The processing module 208 can also parse the physiological data 216 to identify certain characteristic(s) of the blood glucose level. For example, the processing module 208 may calculate metrics that are critical in guiding diabetes treatment in a personalized manner. These metrics can include time-in-range, glycemic variability, glycemic exposure, hypoglycemia range, hyperglycemia range, etc.

The model module 210 can design a personalized statistical model based on explicit data values included in the physiological data 216. More specifically, the model module 210 can examine the explicit data values to identify a feature indicative of a glycemic characteristic of the subject, and then design the statistical model based on the explicit data values, the feature, the glycemic characteristic, or any combination thereof. In some embodiments, each explicit data value corresponds to a time at which the explicit data value was generated. In such embodiments, the model module 210 may also consider the times (also referred to as "time points") when designing the statistical model. Several different models can be designed by the model module 210.

For example, the model module 210 may be configured to construct a Gaussian process model. In such embodiments, the model module 210 can use a radial basis function kernel designed to capture a correlation timescale and a periodic kernel designed to capture typical periodic patterns (e.g., daily, weekly, or monthly patterns). The radial basis function kernel is typically designed to indicate that the blood glucose level is less likely to change over short time intervals (e.g., several seconds) than long time intervals (e.g., several hours). The periodic kernel, meanwhile, can be designed to ensure that imputed data values conform with a periodic pattern of past explicit data values associated with the subject.

As another example, the model module 210 may be configured to construct a Kalman filtering model (also referred to as "linear quadratic estimation model"). In such embodiments, the model module 210 can track variance values indicative of the uncertainty of the imputed data values. By estimating a joint probability distribution over the imputed data values, the model module 210 can increase imputation accuracy over other techniques that are based on a single measurement. The model module 210 can also update the imputed data values and/or the variance values using a state transition model. The state transition model can be based on ordinary differential equation(s) representing the relevant biological responses. In some embodiments the ordinary differential equation(s) are adaptively personalized based on characteristic(s) of the subject, while in other embodiments the ordinary differential equation(s) are statically programmed based on biological literature.

An example of a potential form for an ordinary differential equation is provided by Makroglou et al. in "Mathematical models and software tools for the glucose-insulin regulatory system and diabetes: an overview," *Applied Numerical Mathematics*, 56(3-4):559-573, 2006; Chervoneva et al. in "Estimation of nonlinear differential equation model for glucose-insulin dynamics in type 1 diabetic patients using generalized smoothing," *The Annals of Applied Statistics*, 8(2):886-904, 2014; and De Gaetano et al. in "Mathematical modeling of the intravenous glucose tolerance test," *Journal of Mathematical Biology*, 40(2):136-168, 2000.

$$\frac{dG}{dt} = -b_1 G - b_4 IG + b_7 + S_G(t) \tag{Eq. 1}$$

$$\frac{dI}{dt} = -b_2 I + \frac{b_6}{b_5} \int_{-\infty}^{t} G(s) e^{\frac{s-t}{b_5}} ds + S_I(t) \tag{Eq. 2}$$

where

G Blood glucose level;

I Blood insulin level;

$S_G$ Rate at which glucose enter the blood due to food consumption;

$S_I$ Insulin injection term; and $b_j$ Various parameters from relevant literature (e.g., $b_4$ may measure insulin sensitivity).

Given the following constraints:

1. All parameters and variables >0.
2. $\min(S_{G,I})=0$.
3. A factor enforcing that $S_{G,I}$ be considered "sparse."

With the definition of an auxiliary variable (X) as $$X = \frac{b_6}{b_5} \int_{-\infty}^{t} G(s) e^{(s-t)/b_5} ds, \tag{Eq. 3}$$

the integro-differential equation specifies in equations 1-2 can be transformed into a simple third-order ordinary differential equation.

$$\frac{dX}{dt} = \frac{b_6}{b_5}G - \frac{1}{b_5}X \quad \text{(Eq. 4)}$$

$$\frac{dI}{dt} = -b_2 I + X + S. \quad \text{(Eq. 5)}$$

The equilibrium solution to equations 4-5 is:

$$\tilde{G} = \frac{-b_1\sqrt{b_1^2 + 4b_4 b_6 b_7 / b_2}}{2b_4 b_6 / b_2} \quad \text{(Eq. 6)}$$

$$\tilde{I} = b_6 \tilde{G} / b_2 \quad \text{(Eq. 7)}$$

$$\tilde{X} = b_6 \tilde{G}. \quad \text{(Eq. 8)}$$

The model module 210 can also apply the statistical model to the explicit data values to impute one or more data values for the physiological state of the subject. For example, if the physiological data 216 includes explicit data values specifying the blood glucose level of the subject over a first time interval, then the model module 210 can impute data values for the blood glucose level of the subject over a second time interval.

The analytics module 212 can perform one or more analytic processes based on the explicit data values and/or the imputed data values. Such action may be performed selectively. For instance, the analytics module may only perform the analytic process(es) responsive to discovering the imputed data values are indicative of bad glycemic health, good glycemic health, a downward trend in glycemic health, an upward trend in glycemic health, etc. Examples of analytic processes include prioritizing recommendations provided for improving the glycemic health state of the subject, examining glucose-related metrics critical in guiding diabetes treatment in a personalized manner, filtering certain explicit data values from the physiological data 216 examined by the diabetes management platform 200, etc.

Thus, the analytics module 212 may parse the explicit data values to determine the glycemic health state of the subject. Similarly, the analytics module 212 may parse the imputed data values to predict the future glycemic health state of the subject. Such action may permit the analytics module 212 to identify whether the imputed data values are similar to, or dissimilar from, a target data series corresponding to a healthy glycemic state. The target data series may be a baseline representing the blood glucose levels and the glycemic responses considered to be normal by the American Diabetes Association (ADA). The target data series may correspond to the actual blood glucose measurements of an individual without diabetes. Alternatively, the target data series may be fabricated based on the glycemic range known to be indicative of a healthy glycemic state. Thus, the analytics module 212 can estimate the future glycemic state of the subject based on explicit data values previously generated by a glucose monitoring device.

Figure 3:
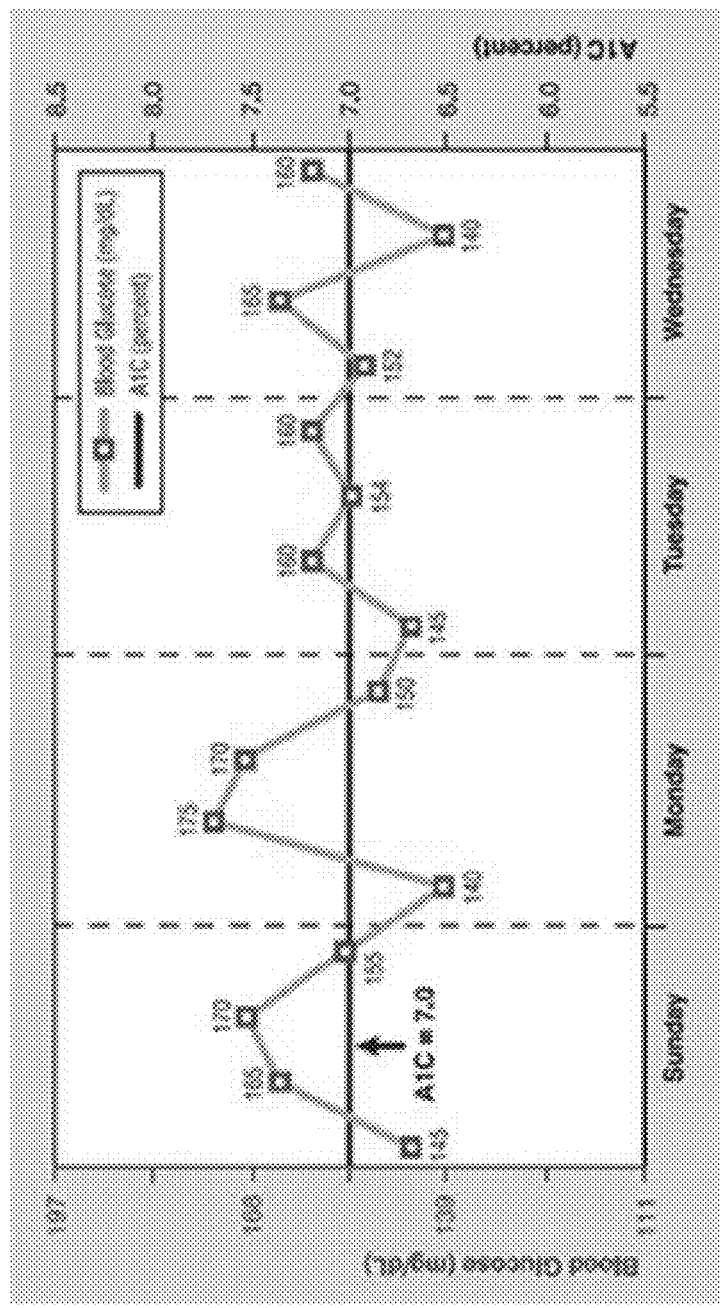
FIG. 3 depicts a series of measurements generated during administrations of A1c test over the course of several days.

The A1c test provides information about the average blood glucose level of a subject. The A1c test may also be referred to as the hemoglobin A1c, HbA1c, or glycohemoglobin test. FIG. 3 depicts a series of measurements generated during administrations of A1c test over the course of several days. The blood glucose level will increase following the ingestion of a foodstuff, and then steadily decrease thereafter. Foodstuffs having a high glycemic index are more rapidly digested, and thus cause substantial fluctuations in the blood glucose level over a short period of time.

According to the ADA, a normal blood glucose level for people without diabetes is below 6.9 mmol/L (125 mg/dL). Meanwhile, the target blood glucose range for people with diabetes is 5.0-7.2 mmol/L (90-130 mg/dL) before meals and less than 10 mmol/L (180 mg/dL) after meals. However, some people with diabetes struggle to consistently stay within the recommended range. For example, individuals with blood glucose levels that are consistently above 7.0 mmol/L (126 mg/dL) are generally considered to have hyperglycemia, while individuals with blood glucose levels that are consistently below 4.0 mmol/L (70 mg/dL) are generally considered to have hypoglycemia.

Visualizations can be helpful in conveying the importance of blood glucose level variations. One example is a glucose trace constructed from a series of measurements generated during administrations of A1c test as shown in FIG. 3. However, because the glucose trace is based on static glucose measurements generated by a blood glucose monitor, the glucose trace can be misleading. For example, past glucose measurements are not necessarily indicative of future glucose measurements. Therefore, direct comparisons of previous time intervals (e.g., consecutive days) are often inaccurate or improper. Moreover, sporadic glucose measurements can make it difficult to draw meaningful conclusions for a time interval. For example, variations in the blood glucose level can easily be overestimated, underestimated, or missed entirely if the subject only performs the A1c test three or four times per day.

Introduced here, therefore, are computer programs and associated computer-implemented techniques for imputing glucose measurements based on explicit glucose measurements generated by a glucose monitoring device. More specifically, a diabetes management platform can enable an intelligent design of a personalized statistical model (also referred to as an "imputation model") for imputing data values for the blood glucose level of a subject.

Figure 4:
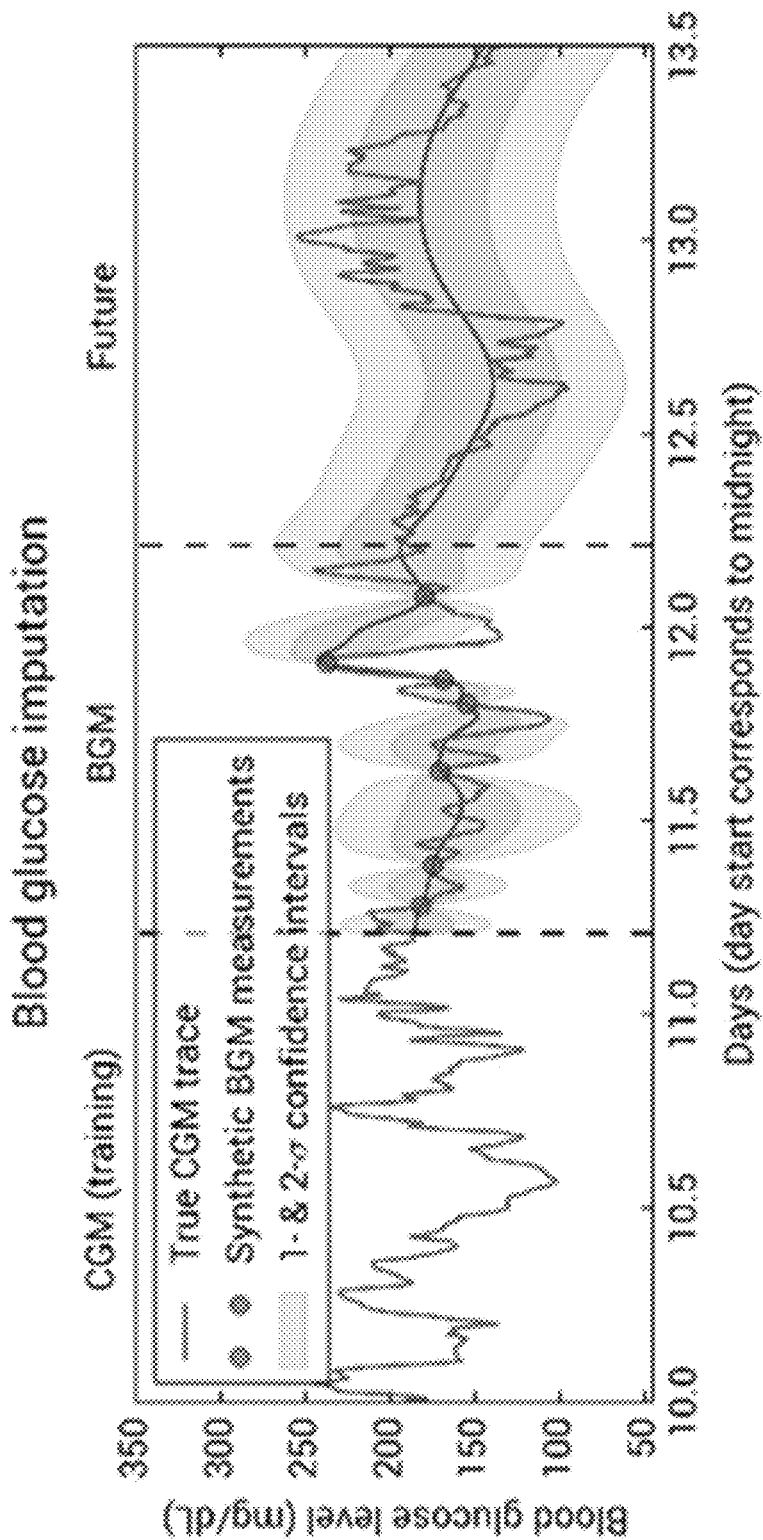
FIG. 4 illustrates how the diabetes management platform can design a statistical model for imputing future glucose measurements based on a first set of explicit glucose measurements included in training data.

FIG. 4 illustrates how the diabetes management platform can design a statistical model for imputing future glucose measurements based on a first set of explicit glucose measurements included in training data. More specifically, FIG. 4 depicts a true glucose trace for a subject. An imputation model has been trained to fit 11 days of physiological data to the left of the first dashed vertical line. Here, the imputation model has also been fed the 7 synthetic data values in the spirit of ad hoc measurements generated by a blood glucose monitor. The gray confidence intervals illustrate where the imputation model believes subsequent data values are likely to reside.

In between the synthetic data values, the imputation model can interpolate the blood glucose level. Consequently, the uncertainty (e.g., represented as the width of the confidence intervals) may increase as the distance from the nearest synthetic data value increases. Outside of the region where these synthetic measurements exist, the imputation model can retreat to previously observed patterns (e.g., daily or weekly patterns).

In general, the diabetes management platform can initially examine explicit glucose measurements during a training period. The glucose monitoring device may be a continuous glucose monitor or a blood glucose monitor. Here, for example, the first set of explicit glucose measurements is generated by a continuous glucose monitor. However, those skilled in the art will recognize that the first set of explicit glucose measurements could additionally or alternatively include values generated by a blood glucose monitor.

The diabetes management platform may also consider a second set of explicit glucose measurements included in training data. Here, for example, the second set of explicit glucose measurements is generated by a blood glucose monitor (BGM) on an ad hoc basis. These explicit glucose measurements are labeled as synthetic BGM measurements in FIG. 4. The diabetes management platform may use the second set of explicit glucose measurements to refine the statistical model, improve the accuracy of imputed glucose measurements, etc. In some instances, the diabetes management platform only examines a single set of explicit glucose measurements (e.g., either the first set of explicit glucose measurements or the second set of explicit glucose measurements) when designing the statistical model.

Each set of explicit glucose measurements may be associated with a different time interval. For example, the first set of explicit glucose measurements may correspond to a first time interval and the second set of explicit glucose measurements may correspond to a second time interval. These time intervals may be directly adjacent to one another as shown in FIG. 4.

The diabetes management platform can use the explicit glucose measurements to impute glucose measurements for a future time interval. For example, the diabetes management platform may examine explicit glucose measurements generated by a blood glucose monitor, and then create a visualization of imputed glucose measurement(s) for review by an individual. The individual may be the subject whose blood glucose level is being monitored or a health coach responsible for monitoring the blood glucose level of the subject.

Figure 5A:
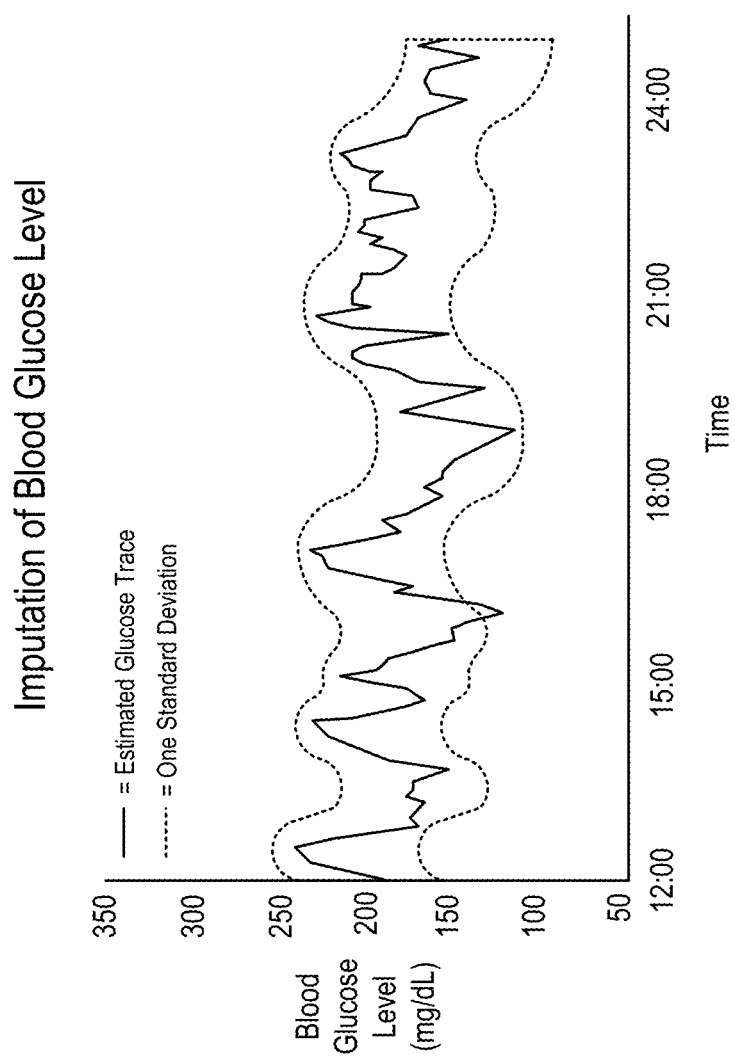
FIG. 5A depicts a visualization of imputed data values that includes a glucose trace and a single error bar.

In some embodiments, the visualization specifies the predicted blood glucose level at a specific time (e.g., "The blood glucose level is expected to be approximately 180 mg/dL at 12 PM."). In other embodiments, the visualization is a glucose trace that is indicative of an approximation of continuous monitoring of the blood glucose level. Thus, the glucose trace based on the imputed glucose measurement(s) may predictively mimic continuous monitoring by a continuous glucose monitor. The visualization may also include a bar plot showing the estimated blood glucose level of a time interval during which the subject hasn't yet taken an explicit glucose measurement. The bar plot may include one or more error bars overlaying the glucose trace. These error bar(s), which can correspond to different confidence interval(s), visually illustrate where the diabetes management platform expects imputed data values to reside. FIG. 4, for example, includes a first error bar corresponding to a confidence interval of one standard deviation and a second error bar corresponding to a confidence interval of two standard deviations. FIG. 5A, meanwhile, includes a single error bar corresponding to a confidence interval of one standard deviation.

Generally, training of the statistical model occurs before execution of the imputation process. Training can be done in several different ways.

For example, the diabetes management platform may examine a dataset for an individual corresponding to a past time interval. In such embodiments, the diabetes management platform could train the statistical model on the dataset, and then impute values for an upcoming time interval.

As another example, the diabetes management platform may examine a dataset for an individual that includes a first subset (e.g., for a morning time interval) and a second subset (e.g., for an evening time interval). In such embodiments, the diabetes management platform could train the statistical model on the first subset, and then impute additional values for the first subset. Additionally or alternatively, the diabetes management platform could train the statistical model on the first subset, and then impute additional values for the second subset.

As another example, the diabetes management platform may examine a first dataset for a first individual and a second dataset for a second individual. These individuals may share a characteristic in common, such as age, ethnicity, activity level, diabetes classification, etc. In such embodiments, the diabetes management platform could train the statistical model on the first dataset, and then impute additional values for the second dataset. Because blood glucose level is often highly dependent on the characteristics/circumstances of the corresponding individual, this type of training process may be avoided in favor of more personalized training processes.

Figure 5B:
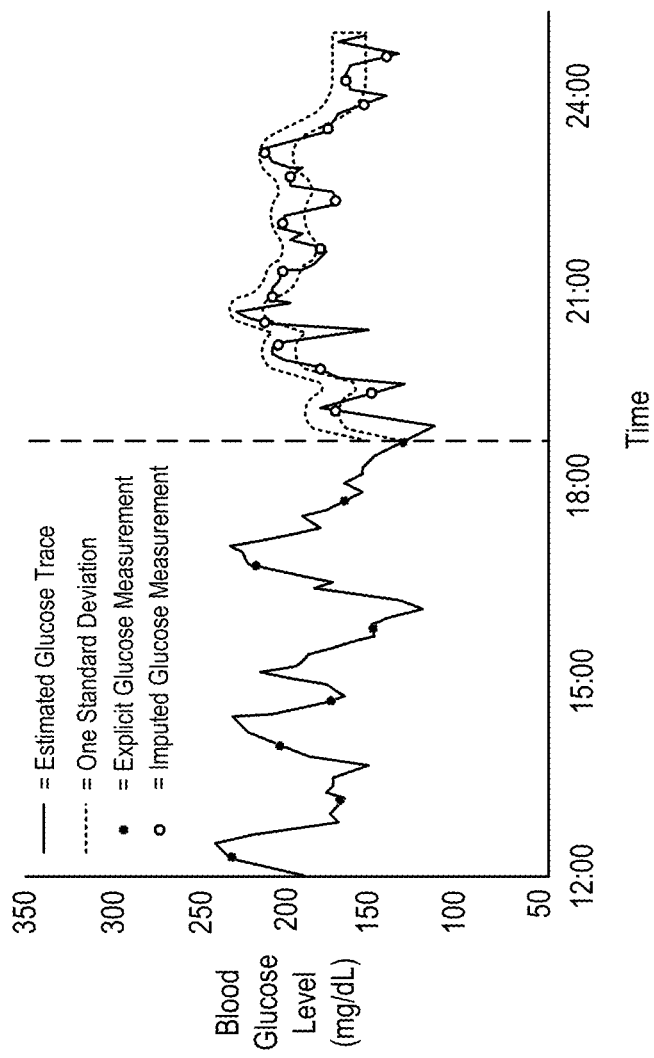
FIG. 5B depicts a visualization of imputed data values that is capable of being dynamically modified as new explicit data values are received.

FIG. 5B illustrates how the diabetes management platform may dynamically modify the bar plot as additional explicit glucose measurements are acquired over time. The diabetes management platform can, upon acquiring a new explicit glucose measurement, modify the bar plot to reflect the increase in certainty of the blood glucose level of the subject. For example, the diabetes management platform may monitor the duration since the most recent explicit glucose measurement. As the duration increases, the diabetes management platform may modify the bar plot by dynamically altering the width of the error bar(s). Increases in the width may be substantially proportional to increases in the duration.

Upon acquiring the new explicit glucose measurement, the diabetes management platform may replace a corresponding imputed glucose measurement with the new explicit glucose measurement. Generally, the corresponding imputed glucose measurement will be the closest past imputed glucose measurement. For example, if the diabetes management platform generates an imputed glucose measurement every half hour on the hour (e.g., 12:00, 12:30, 13:00, etc.), then an explicit glucose measurement taken at 12:55 will correspond to the imputed glucose measurement at 12:30. An explicit glucose measurement may correspond to multiple imputed glucose measurements if the time since the last explicit glucose measurements exceeds the periodicity of the imputed glucose measurements.

In some embodiments, imputed glucose measurements are visually distinguishable from explicit glucose measurements. In other embodiments, only imputed glucose measurements or explicit glucose measurements may be visible. For example, a visualization may include a visual representation of each explicit glucose measurement and an estimated glucose trace indicative of the imputed glucose measurements.

The diabetes management platform may also dynamically collapse the error bar(s) to indicate an increase in certainty of the blood glucose level due to the acquisition of the new explicit glucose measurement. Such action can incentivize subjects to administer the A1c test more frequently, thereby providing health coaches with more data to use when coaching the subjects. These techniques can be used in addition to, or instead of, conventional incentive techniques (e.g., affirmative messages and graphical illustrations of balloons/confetti/etc.).

Those skilled in the art will recognize that some individuals may prefer to see a mix of explicit and imputed glucose measurements (as shown in FIG. 5B), while other individuals may prefer to see only imputed glucose measurements for upcoming time intervals (as shown in FIG. 5A).

FIG. 6 depicts a flow diagram of a process 600 for producing a statistical model for probabilistically imputing data values where explicit data values have not been generated. These imputed data values may be used to guide an individual toward a healthier glycemic state. For example, a diabetes management platform may examine the imputed data values to discover they are indicative of healthy or unhealthy blood glucose measurements. Such action may permit the diabetes management platform to recommend certain actions be performed or refrained from during an upcoming time interval.

Initially, the diabetes management platform acquires multiple explicit data values representing static measurements of the blood glucose level of a subject (step 601). Each explicit data value may correspond to a different time point. Thus, the diabetes management platform may construct a data series from the explicit data values that includes discrete, digitally-represented values in a temporal order that are indicative of time-varying glucose concentration sampled on an ad hoc basis.

The diabetes management platform can then examine the explicit data values to identify a feature indicative of a glycemic characteristic of the subject (step 602). The glycemic characteristic may be, for example, diabetes classification, blood glucose level trend(s) over certain time period(s), periodicity of the explicit data values, maximum data value, minimum data value, etc. The diabetes management platform can design a statistical model based on the explicit data values, the corresponding time points, the glycemic characteristic, or any combination thereof (step 603).

For example, the statistical model may be a Gaussian process model. In such embodiments, the diabetes management platform can create a radial basis kernel that indicates the blood glucose level is more likely to vary over long time intervals (e.g., hours) than short time intervals (e.g., seconds) and a periodic kernel that ensures any imputed data values conform with a periodic pattern of past explicit data values. The periodic pattern may be based on a series of past explicit data values taken over the course of a day, week, month, etc.

As another example, the statistical model may be a Kalman filtering model. In such embodiments, the diabetes management platform can, for each imputed data value, produce an estimated value indicative of the predicted blood glucose level at a future time, generate a variance measure indicative of the uncertainty of the estimated value, and periodically update the estimated value or the variance measure using a state transition model. The state transition model can be based on ordinary differential equation(s) representing the relevant biological responses. In some embodiments the ordinary differential equation(s) are adaptively personalized based on biological characteristic(s) of the subject, while in other embodiments the ordinary differential equation(s) are statically programmed based on biological literature.

The diabetes management platform can then apply the statistical model to the explicit data values to impute one or more data values for a future time interval where explicit data values have not been generated (step 604). Such action may require the diabetes management platform perform interpolation and/or extrapolation. Thus, for each imputed data value, the diabetes management platform can either interpolate the imputed data value from at least one explicit data value located within a certain proximity or extrapolate the imputed data value from a periodic pattern responsive to a determination that no explicit data values exist within the certain proximity. The certain proximity may be automatically determined by the diabetes management platform and/or manually specified by an individual. The certain proximity could be 30 minutes, 1 hour, 2 hours, 4 hours, etc.

Thus, the diabetes management platform may interpolate the blood glucose level between explicit data values taken on an ad hoc basis and extrapolate blood glucose level where no explicit data values exist. For example, if a Gaussian process is used for imputation, then the diabetes management platform can use as a kernel the sum of a Matérn kernel and a periodic kernel. The periodic kernel may have a fixed period of 24 hours to capture/learn daily patterns of the subject. Thus, in some instances a statistical model may revert to previously observed daily patterns due to enforcement of a 1-day-periodicity Gaussian process kernel. A series of imputed data values can include both interpolated data values and extrapolated data values.

In some embodiments, the diabetes management platform constructs a data series that includes the explicit data values and/or the imputed data values (step 605). The data series may be indicative of an approximation of continuous monitoring of the time-varying blood glucose level of the subject. The diabetes management platform may also store the explicit and imputed data values in separate data series. Thus, the explicit data values may be stored in a first data series and the imputed data values may be stored in a second data series. The diabetes management platform can store the data series in a database record associated with a subject profile (step 606). Additionally or alternatively, the diabetes management platform may store certain explicit/imputed data values in the subject profile. For example, the diabetes management platform may track the maximum and/or minimum value within a certain timeframe (e.g., a day, week, or month) or across the subject's entire history with the diabetes management platform. As another example, the diabetes management platform may track mean glucose, which could be updated over time as additional explicit data values are acquired.

Figure 7:
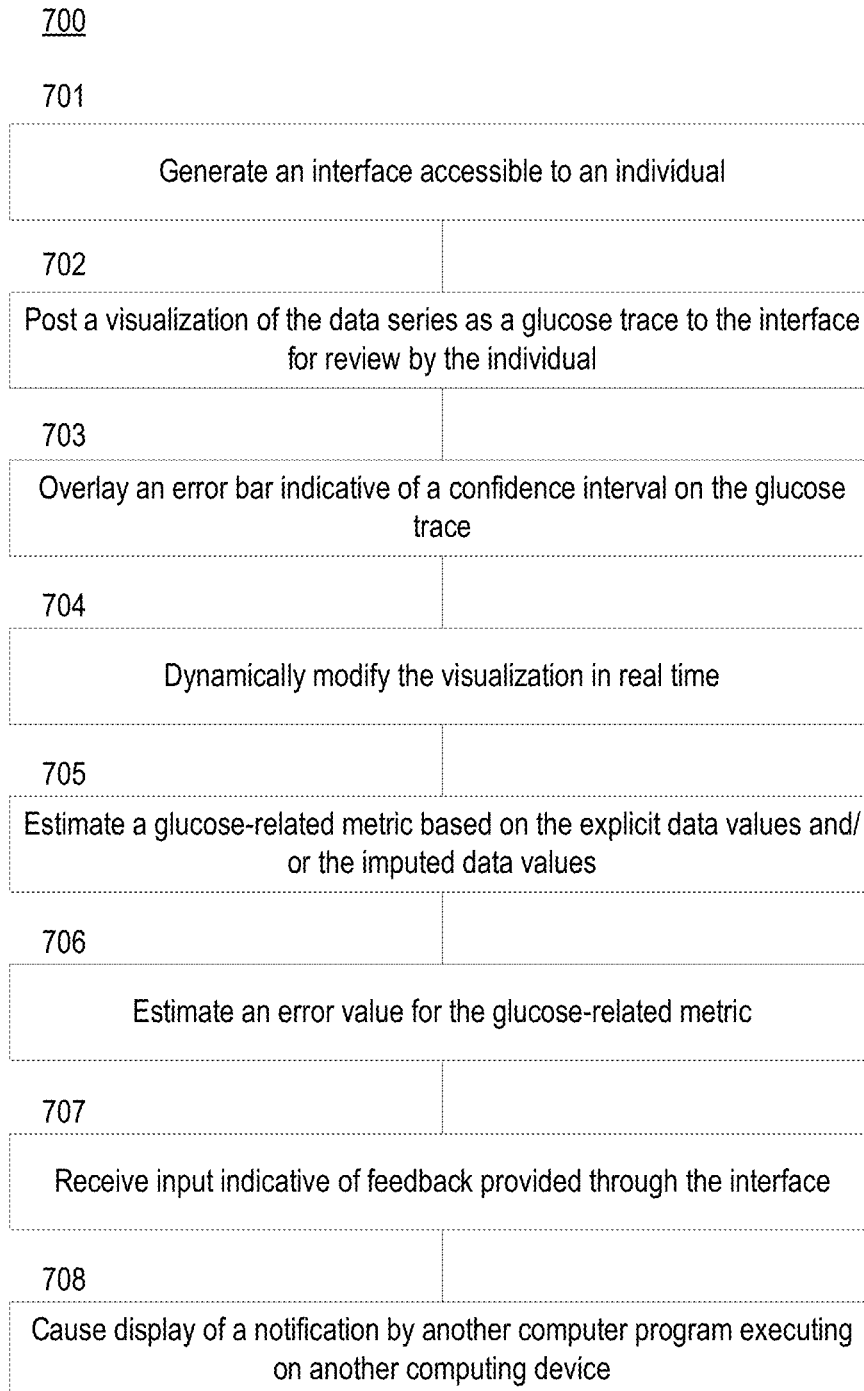
FIG. 7 depicts a flow diagram of a process for communicating the results of the process of FIG. 6 to an individual.

FIG. 7 depicts a flow diagram of a process 700 for communicating the results of process 600 to an individual. In some embodiments the individual is a person with diabetes, while in other embodiments the individual is interested in examining physiological data associated with some other person. Thus, the individual may be a health coach such as a medical professional (e.g., a physician or nurse), a diabetic health counselor, a family member, etc.

Initially, a computer program executing on a computing device will generate an interface accessible to an individual (step 701). The computer program can then post a visualization of the data series as a glucose trace over time to the interface for review by the individual (step 702). The visualization can take several different forms. For example, FIG. 4 depicts a visualization that includes a glucose trace and multiple error bars corresponding to different confidence intervals. As another example, FIG. 5A depicts a visualization that includes a glucose trace and a single error bar. As another example, FIG. 5B depicts a visualization capable of being dynamically modified as new explicit data values are received.

As noted above, the computer program may overlay an error bar indicative of a confidence interval on the glucose trace (step 703). The error bar may correspond to one standard deviation, two standard deviations, etc. In some embodiments, the error bar is one of multiple error bars corresponding to different confidence intervals (e.g., 1-$\sigma$ confidence interval, 2-$\sigma$ confidence interval, etc.).

In some embodiments, the computer program is configured to dynamically modify the visualization in real time (step 704). For example, upon acquiring a new explicit data value, the computer program may collapse the error bar to indicate an increase in the certainty of the time-varying blood glucose level due to the new explicit data value. As another example, the computer program may monitor the duration since the most recent explicit data value was received, and then modify the visualization based on the duration. More specifically, the computer program can adaptively alter the width of the error bar. Generally, the width of the error bar will increase as the duration increases (and thus confidence decreases) and decrease as the duration decreases (and thus confidence increases).

The computer program can estimate a glucose-related metric based on the explicit data values and/or the imputed data values (step 705). Examples of glucose-related metrics include time-in-range, mean glucose, day-estimated A1c level, standard deviation of the blood glucose level, coefficient of variation of the blood glucose level, etc. The computer program may post the glucose-related metric to the interface for review by the individual, store the glucose-related in a database record associated with a subject profile, etc.

In some embodiments, the computer program also estimates an error value for the glucose-related metric (step 706). The error value can also be posted to the interface for review by the individual, stored in the database record associated with the subject profile, etc.

If the individual is a health coach responsible for monitoring the glycemic health of another person (also referred to as a "subject" or "patient"), then the computer program may receive input indicative of feedback provided through the interface (step 707). The feedback may include a recommendation for improving the subject's glycemic health. For example, the health coach may identify certain activities or foodstuffs that are associated with a decline in glycemic health, and thus should be avoided. As another example, the health coach may identify certain activities or foodstuffs that are associated with an improvement in glycemic health, and thus should be performed. In such embodiments, the computer program may cause display of a notification by another computer program executing on another computing device associated with the subject (step 708). For example, the computer program may communicate directly with the other computer program through a simple messaging technology. As another example, the computer program may transmit the notification to a diabetes management platform, which may be responsible for forwarding the notification to the other computer program.

Other steps may also be performed. For example, if the individual is the subject whose blood glucose level is being monitored, then the computer program may automatically display a recommendation for improving the glycemic health state. Thus, the recommendation may not be based on feedback provided by a health coach. Instead, the computer program could dynamically identify appropriate feedback based on the explicit data values and/or the imputed data values. As another example, the computer program may determine an accuracy measure for the statistical model upon acquiring a new explicit data value. The accuracy measure may be discovered by comparing the new explicit data value to a corresponding imputed data value. The computer program may alter the statistical model responsive to a determination that the accuracy measure falls below a threshold.

The computer program may also enable a health coach to perform other action(s). For example, the health coach may be able to make an annotation that is dynamically linked to an explicit data value or an imputed data value. Generally, the annotation is subsequently presented to the subject for review. However, the annotation may not be shown to the subject (e.g., in instances where the health coach flags an imputed data value to be examined more closely for accuracy). As another example, the health coach may be able to generate a comparison of the imputed data values and the explicit data values corresponding to the same interval. The comparison can permit the health coach to visually observe accuracy in estimating the blood glucose level over time.

Moreover, the computer program may enable the health coach to compile visualization component(s) using the explicit data values, the imputed data values, etc. The visualization component(s) could include text, audio, video, or any combination thereof. Some visualization components only include text specifying a recommendation for improving glycemic health, while other visualization components include audio and/or video for incentivizing future performance of certain activities (e.g., compliance with a testing regimen may be incentivized by showing digital balloons, confetti, etc.). As another example, the computer program may identify actual trends in the blood glucose level by examining the explicit data values. Such trends may indicate whether the glycemic health of the subject is improving or declining over time. Similarly, the computer program may identify predicted trends in the blood glucose level by examining the imputed data values. Such trends may indicate whether the glycemic health of the subject is expected to improve or decline over time.

Unless contrary to physical possibility, it is envisioned that the steps described above may be performed in various sequences and combinations. For example, the diabetes management platform may simultaneously notify a subject whose blood glucose level is being monitored and a health coach responsible for monitoring the glycemic health of the subject. As another example, the diabetes management platform may periodically execute these processes such that imputed data values are generated on a periodic basis (e.g., daily, weekly, or monthly).

Other steps may also be included in some embodiments. For example, the diabetes management platform may perform an analytic process on the explicit data values and/or the imputed data values to estimate the glycemic health state of the subject. Such action may be performed selectively. For instance, the diabetes management platform may only perform the analytic process responsive to discovering the imputed data values are indicative of bad/good glycemic health. Examples of analytic processes include prioritizing recommendations provided for improving the glycemic state of the subject, examining glucose-related metrics critical in guiding diabetes treatment in a personalized manner, posting certain glucose-related metrics and/or visualizations to an interface for review by the subject or a health coach, etc.

Use Cases

Interfaces produced by the diabetes management platform introduced here allow subjects to readily monitor their own blood glucose levels. More specifically, consistent use of these interfaces over time enable subjects to better control their diabetes, as well as improve their overall state of health. Several different use cases illustrate the benefits provided by the diabetes management platform.

First, the diabetes management platform may produce a visualization that includes a bar plot showing the estimated blood glucose level of a time interval during which the subject hasn't yet taken an explicit glucose measurement. As shown in FIGS. 4-5B, the bar plot may include one or more error bars overlaying the glucose trace. These error bar(s), which correspond to different confidence interval(s), visually illustrate where the diabetes management platform expects imputed data values to reside.

The diabetes management platform can be configured to dynamically collapse the error bar(s) to indicate an increase in certainty of the blood glucose level upon receiving new explicit glucose measurements. More specifically, when the subject fails to generate an explicit glucose measurement, the uncertainty will increase (and thus the confidence interval will widen). However, when an explicit glucose measurement is acquired, the confidence interval can collapse, thereby indicating that the diabetes management platform knows the blood glucose level with certainty.

Such action can incentivize subjects to generate more frequent explicit glucose measurements, thereby providing health coaches with more data to use when coaching the subjects. These techniques can be used in addition to, or instead of, conventional incentive techniques (e.g., affirmative messages and graphical illustrations of balloons/confetti/etc.).

Second, the diabetes management platform may compute glucose-related metrics that are critical in guiding diabetes treatment in a personalized manner. Computing these metrics is non-trivial when using blood glucose monitoring data generated by a blood glucose monitor since coverage is low (e.g., glucose measurements are taken sporadically on an ad hoc basis). However, these metrics can be readily computed using imputed data value(s) generated by the statistical models introduced here. Moreover, the statistical models can compute estimates of the error of each metric.

Third, given a statistical model, the diabetes management platform can generate intelligent recommendations for improving the glycemic health of the subject, increasing accuracy of imputed data values, etc. For example, the diabetes management platform may be able to identify the number of explicit data values that should be generated, as well as the times at which those explicit data values should be generated, to minimize the error of a given glucose-related metric. An example of a technique for discovering the optimal sampling frequency is provided below.

Assume the diabetes management platform has applied a Gaussian process model to create a set of glucose measurements ($y_d$) at a certain number ($n_d$) of time points ($t_d$) having an appropriate covariance kernel (K). The diabetes management platform may wish to determine the optimal number ($n_s$) of time points ($t_s$) at which new measurements should be taken over some time interval ($T_s$) such that the variance of an integral $$I = \int_{T_g} f(y) dt \quad \text{(Eq. 9)}$$

over a potentially different time interval ($T_g$) is minimized. The diabetes management platform can approximate this integral with a grid of $n_g$ time points ($t_g$) using, for example, $$I(y_g) \approx \frac{1}{n_g \Delta t} \sum f(y_g), \quad \text{(Eq. 10)}$$

where $y_g$ is a vector of random variables. An alternate integration rule could be readily substituted as I may be an arbitrary scalar function of $y_g$.

The mean of $I(y_g)/y_d, y_s$ across all values of $y_g$ is $$\langle I \rangle_{g|ds} = \int I(y_g) P_{g|ds} dy_g, \quad \text{(Eq. 11)}$$

where the diabetes management platform can denote, for example, $P_{g/ds} \equiv P(y_g/y_d, y_s)$.

Next, the variance of $I(y_g)/y_d, y_s$ is $$\text{var}_{g|ds}(I) = \langle I^2 \rangle_{g|ds} - \langle I \rangle^2_{g|ds}. \quad \text{(12)}$$

The diabetes management platform can then take the expectation value over all $y_s$ $$V \equiv \langle \text{var}_{g|ds}(I) \rangle_{s|d} = \quad \text{(Eq. 13)}$$

$$\int \int I^2 P_{g|ds} P_{s|d} dy_g dy_s - \int \left( \int I P_{g|ds} dy_g \right)^2 P_{s|d} dy_s =$$

$$\int \int I^2 P_{gs|d} dy_g dy_s -$$

$$\int \int \int I I' P_{g|ds} P_{g'|ds} P_{s|d} dy_g dy'_g dy_s =$$

$$\int I^2 P_{g|d} dy_g -$$

$$\int \int \int \left( \frac{I I' P_{s|dg}}{P_{s|d}} \right) P_{g'|sd} P_{g|d} dy'_g dy_s dy_g =$$

$$\langle I^2 \rangle_{g|d} - \left\langle I' \left\langle I \frac{P_{s|dg}}{P_{s|d}} \right\rangle_{g|d} \right\rangle_{g'|sd}$$

The diabetes management platform can drop the first term since it does not affect optimization of V with respect to $t_s$. Each expectation value can be evaluated by sampling from the appropriate Gaussian. The diabetes management platform can then minimize V with respect to $t_s$ to find the optimal sampling points. Sampling at each optimization step can be avoided by sampling over a grid spanning $T_g \cup T_s$ once, and then interpolating at each optimization step to find samples of $y_s$ given $t_s$.

The probability quotient evaluated to $$\frac{P_{s|dg}}{P_{s|d}} = \sqrt{\frac{|Q_d|}{|Q_{dg}|}} \exp(-z_{dg} + z_d) \quad \text{(Eq. 14)}$$

where $$z_x(y_s - \mu_x) Q_x^{-1}(y_s - \mu_x) \quad \text{(Eq. 15)}$$

$$Q_s = K_{ss} - C_x B_x^{-1} C_x^T \quad \text{(Eq. 16)}$$

$$\mu_d = C_d B_d^{-1} y_d \quad \text{(Eq. 17)}$$

$$\mu_{dg} = C_{dg} B_{dg}^{-1} \begin{bmatrix} y_d \\ y_g \end{bmatrix} \quad \text{(Eq. 18)}$$

and $$B_d = K_{dd} \quad B_{dg} = \begin{bmatrix} K_{dd} & K_{dg} \\ K_{gd} & K_{gg} \end{bmatrix} \quad C_d = K_{sd} \quad C_{dg} = [K_{sd} \quad K_{sg}] \quad \text{(Eq. 19)}$$

and, for example, $K_{dg} = K(t_d, t_g)$.

Probabilistic Estimation of Glucose-Related Metrics

Possessing an imputation model enables a diabetes management platform to probabilistically evaluate integrals that provide aggregate measures indicative of the severity of the diabetes disease state using only measurements generated by a blood glucose monitor (i.e., blood glucose monitoring data). Without an imputation model, it is difficult to account for the fact that measurements may be temporally clustered, or that some time intervals may be poorly sampled (e.g., while the subject is asleep).

In the confidence interval plot of FIG. 4, several metrics were computed over the "BGM" time interval (i.e., between the two dashed vertical lines). These metrics are included in Table I.

TABLE I

Probabilistic estimation of time-in-range, HbA1c, and other glucose metrics.

| Metric | Imputation Value | Standard Error (1-σ) | True Value from CGM |
|---|---|---|---|
| Time-In-Range (%) | 54 | 10 | 71 |
| Mean Glucose (mg/dL) | 180 | 8 | 171 |
| Day-Estimated A1c (%) | 7.9 | 0.3 | 7.6 |
| Standard Deviation (mg/dL) | 31 | 6 | 29 |
| Coefficient of Variation | 0.17 | 0.03 | 0.17 |

Figure 8:
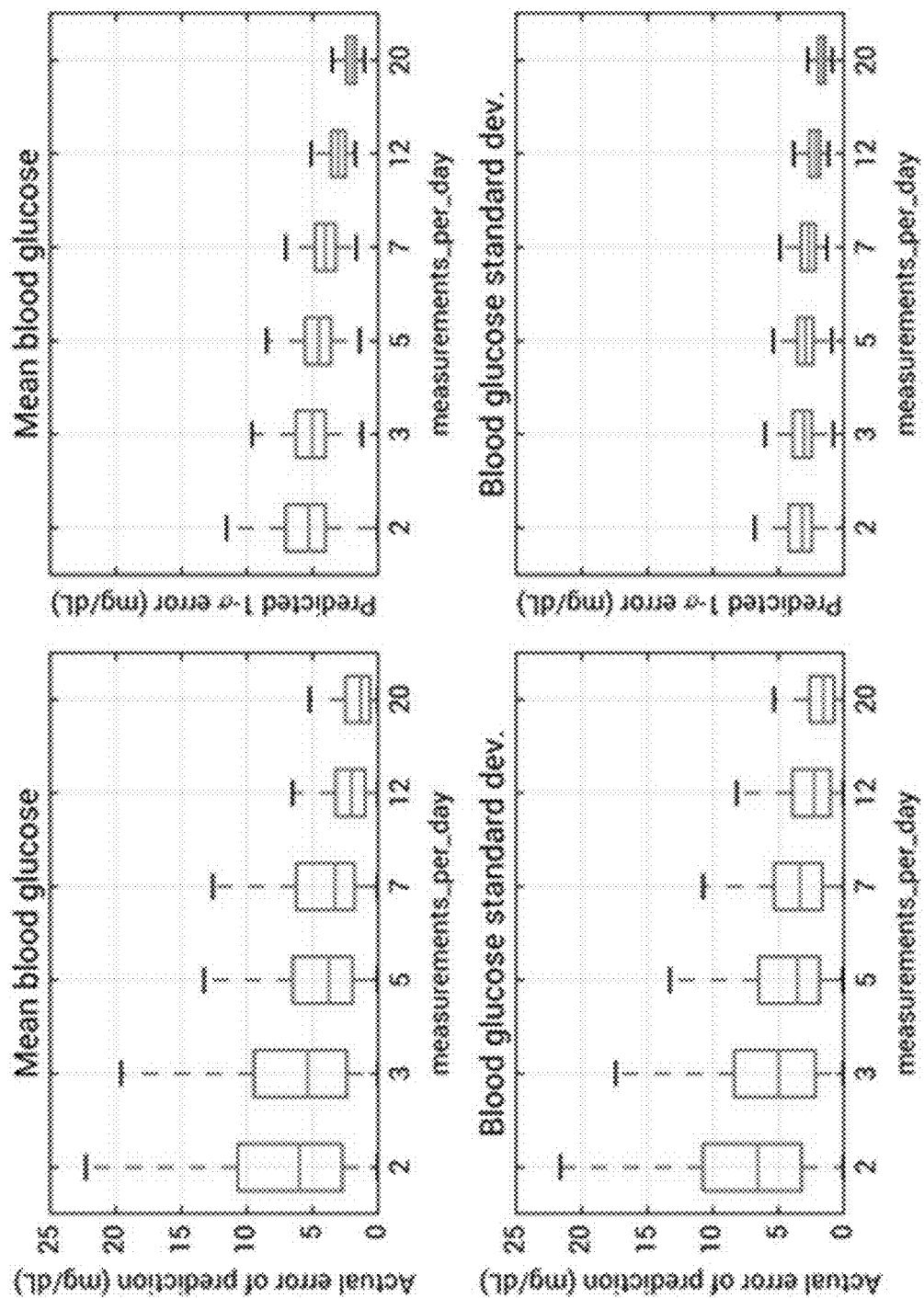
FIG. 8 depicts the measured errors (from comparing to the continuous glucose monitoring data) and predicted errors (from sampling, for example, the Gaussian process model) for several glucose-related metrics.

The imputation model can also be trained using synthetic data values in the spirit of ad hoc measurements generated by a blood glucose monitor. That is, an imputation model can be trained without any continuous glucose monitoring data. The number of synthetic data values included in a certain time interval (e.g., a 24-hour period) can vary. For example, the number of synthetic data values may be randomly distributed across 10 training days. A diabetes management platform can then investigate the resulting errors in predicting glucose-related metrics, such as the mean glucose and glucose standard deviation (which is a measure of glycemic variability). More specifically, the diabetes management platform can compare the predicted glucose-related metrics to those actually measured by examining corresponding continuous glucose monitoring data. The measured errors (from comparing to the continuous glucose monitoring data) and predicted errors (from sampling, for example, the Gaussian process model) are shown in FIG. 8.

The median errors track reasonably well in most instances. However, there are some instances in which large errors occur that are inconsistent with the predicted error from the Gaussian process.

FIG. 9 is an alternate visualization for when the number of measurements per day is seven. Note that several points exist whose error bars do not intersect the dashed line. This can also be seen with the $\chi^2$ values, which are greater than one (but would ideally be approximately one). The diabetes management platform could, for example, multiple the predicted errors derived from sampling the Gaussian process by a per-metric factor in order to produce a $\chi^2$ of appropriately 1. For example, multiplying by approximately two would achieve this for the standard deviation shown in FIG. 9.

Figure 10:
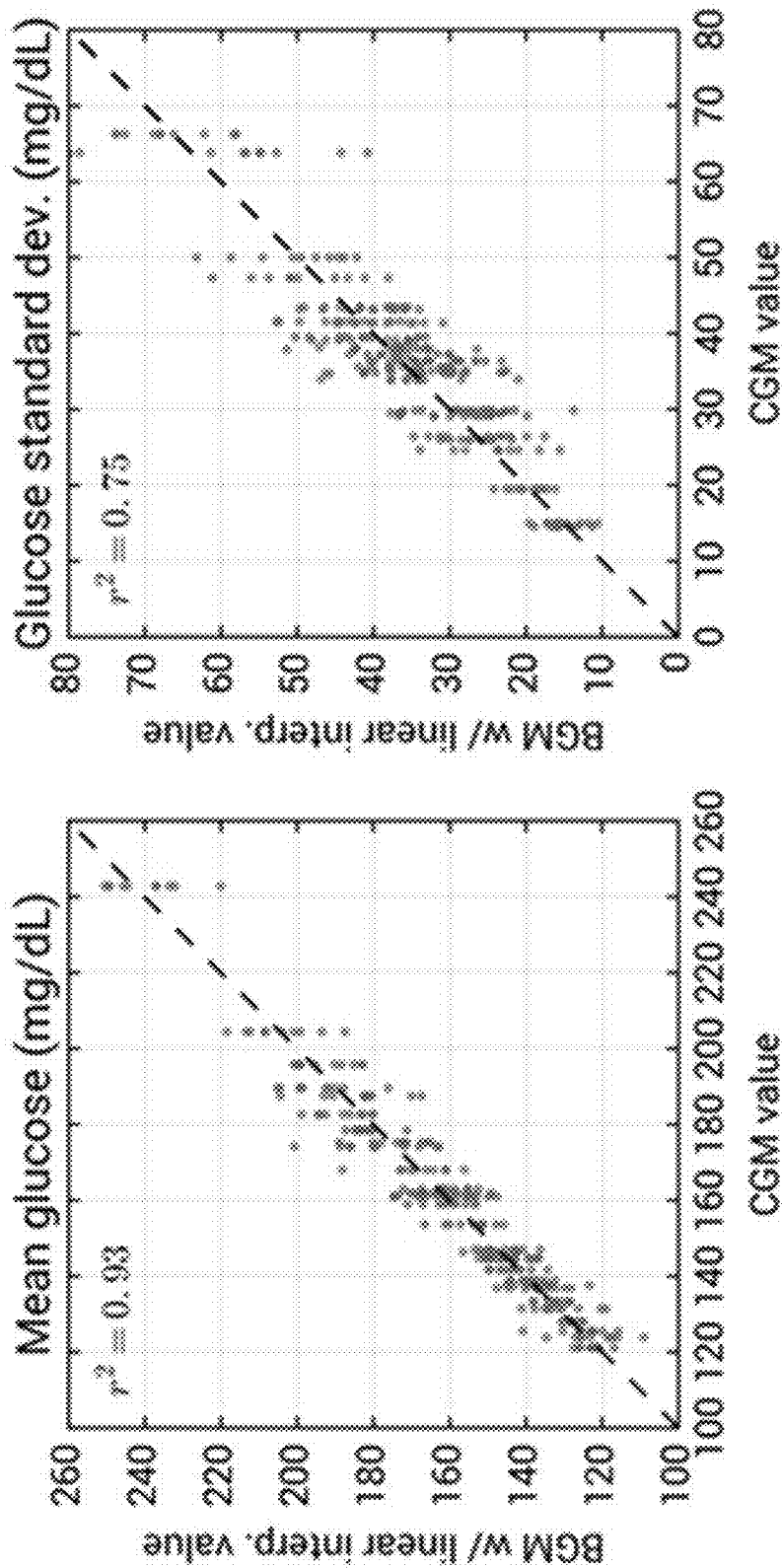
FIG. 10 depicts the results of computing similar glucose-related metrics in a more static manner.

The diabetes management platform can also compare these results to a static manner of computing the same metrics (e.g., linearly interpolating between the synthetic data values, and then computing means and standard deviations on top of the interpolants). FIG. 10 depicts the results of such a static manner of computing metrics. The results are worse than the Gaussian process-based methods in terms of $r^2$ and does not naturally produce error estimates, though it is substantially simpler from the design and resource consumption perspectives.

Processing System

Figure 11:
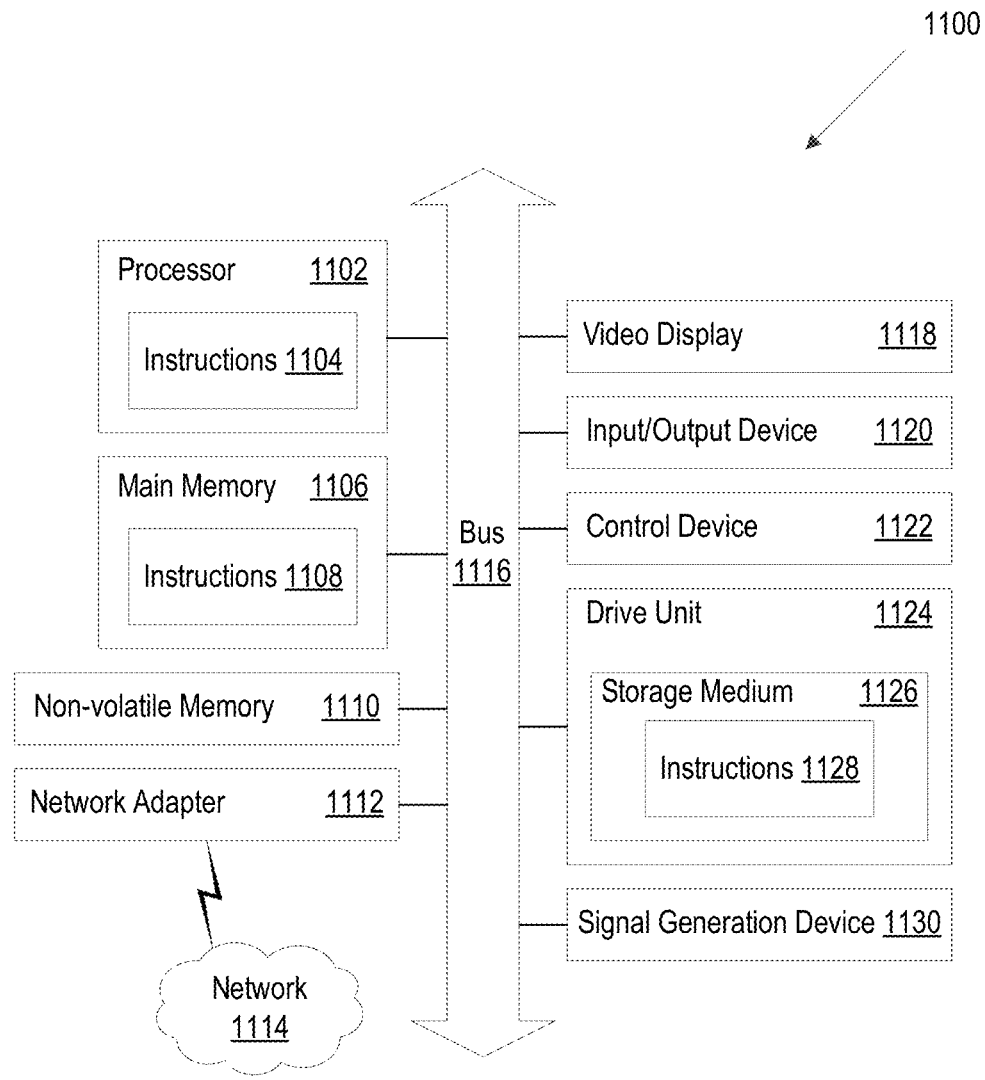
FIG. 11 is a block diagram illustrating an example of a processing system in which at least some operations described herein can be implemented.

FIG. 11 is a block diagram illustrating an example of a processing system 1100 in which at least some operations described herein can be implemented. For example, some components of the processing system 1100 may be hosted on a computing device that includes a diabetes management platform (e.g., diabetes management platform 102 of FIG. 1).

The processing system 1100 may include one or more central processing units ("processors") 1102, main memory 1106, non-volatile memory 1110, network adapter 11281112 (e.g., network interface), video display 1118, input/output devices 1120, control device 1122 (e.g., keyboard and pointing devices), drive unit 1124 including a storage medium 1126, and signal generation device 1130 that are communicatively connected to a bus 1116. The bus 1116 is illustrated as an abstraction that represents one or more physical buses and/or point-to-point connections that are connected by appropriate bridges, adapters, or controllers. The bus 1116, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The processing system 1100 may share a similar computer processor architecture as that of a desktop computer, tablet computer, personal digital assistant (PDA), mobile phone, game console, music player, wearable electronic device (e.g., a watch or fitness tracker), network-connected ("smart") device (e.g., a television or home assistant device), virtual/augmented reality systems (e.g., a head-mounted display), or another electronic device capable of executing a set of instructions (sequential or otherwise) that specify action(s) to be taken by the processing system 1100.

While the main memory 1106, non-volatile memory 1110, and storage medium 1126 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 1128. The term "machine-readable medium" and "storage medium" shall also be taken to include any medium that is capable of storing, encoding, or carrying a set of instructions for execution by the processing system 1100.

In general, the routines executed to implement the embodiments of the disclosure may be implemented as part of an operating system or a specific application, component, program, object, module, or sequence of instructions (collectively referred to as "computer programs"). The computer programs typically comprise one or more instructions (e.g., instructions 1104, 1108, 1128) set at various times in various memory and storage devices in a computing device. When read and executed by the one or more processors 1102, the instruction(s) cause the processing system 1100 to perform operations to execute elements involving the various aspects of the disclosure.

Moreover, while embodiments have been described in the context of fully functioning computing devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 1110, floppy and other removable disks, hard disk drives, optical disks (e.g., Compact Disk Read-Only Memory (CD-ROMS), Digital Versatile Disks (DVDs)), and transmission-type media such as digital and analog communication links.

The network adapter 11281112 enables the processing system 1100 to mediate data in a network 1114 with an entity that is external to the processing system 1100 through any communication protocol supported by the processing system 1100 and the external entity. The network adapter 11281112 can include a network adaptor card, a wireless network interface card, a router, an access point, a wireless router, a switch, a multilayer switch, a protocol converter, a gateway, a bridge, bridge router, a hub, a digital media receiver, and/or a repeater.

The network adapter 11281112 may include a firewall that governs and/or manages permission to access/proxy data in a computer network and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall may additionally manage and/or have access to an access control list that details permissions including the access and operation rights of an object by an individual, a machine, and/or an application, and the circumstances under which the permission rights stand.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

Remarks

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling those skilled in the relevant art to understand the claimed subject matter, the various embodiments, and the various modifications that are suited to the particular uses contemplated.

Although the Detailed Description describes certain embodiments and the best mode contemplated, the technology can be practiced in many ways no matter how detailed the Detailed Description appears. Embodiments may vary considerably in their implementation details, while still being encompassed by the specification. Particular terminology used when describing certain features or aspects of various embodiments should not be taken to imply that the terminology is being redefined herein to be restricted to any specific characteristics, features, or aspects of the technology with which that terminology is associated. In general, the terms used in the following claims should not be construed to limit the technology to the specific embodiments disclosed in the specification, unless those terms are explicitly defined herein. Accordingly, the actual scope of the technology encompasses not only the disclosed embodiments, but also all equivalent ways of practicing or implementing the embodiments.

The language used in the specification has been principally selected for readability and instructional purposes. It may not have been selected to delineate or circumscribe the subject matter. It is therefore intended that the scope of the technology be limited not by this Detailed Description, but rather by any claims that issue on an application based hereon. Accordingly, the disclosure of various embodiments is intended to be illustrative, but not limiting, of the scope of the technology as set forth in the following claims.

What is claimed is:

1. A computer-implemented method comprising:
   acquiring multiple explicit data values generated by a blood glucose meter that measures a time-varying blood glucose level of a subject on an ad hoc basis,
      wherein each explicit data value of the multiple explicit data values is a discrete, digitally-represented value indicative of the time-varying blood glucose level at a corresponding time point in a first time interval;
   computing, based on the multiple explicit data values, a digitally-represented feature indicative of a glycemic characteristic of the subject;
   applying a Gaussian process model to the multiple explicit data values to impute one or more data values for the time-varying blood glucose level of the subject,
      wherein each imputed data value of the one or more imputed data values corresponds to a time point in a second time interval at least partially different from the first time interval;
   constructing a data series that includes the multiple explicit data values and the one or more imputed data values,
      wherein the data series represents a simulation of measurements generated by a continuous glucose monitor of the time-varying blood glucose level over the first and second time intervals; and
   posting a visualization of the data series as a glucose trace over time to an interface generated by a computer program executing on a computing device associated with an individual.

2. The computer-implemented method of claim 1, further comprising:
   configuring a Gaussian process model based on the multiple explicit data values, the multiple corresponding time points, the digitally-represented feature, or any combination thereof; and
   training the Gaussian process model using a training set of explicit data values,
      wherein the training set of explicit data values includes the multiple explicit data values, other explicit data values, or any combination thereof.

3. The computer-implemented method of claim 1, wherein the one or more imputed data values are visually distinguishable from the multiple explicit data values in the glucose trace posted to the interface.

4. The computer-implemented method of claim 1, said applying comprises:
   for each imputed data value of the one or more imputed data values,
      interpolating the imputed data value from at least one explicit data value within a specified proximity, or extrapolating the imputed data value from a periodic pattern responsive to a determination that no explicit data values exist within the specified proximity.

5. The computer-implemented method of claim 4, wherein the periodic pattern is based on a series of explicit data values generated by the glucose monitoring device over the course of a natural cycle of a person or a mammalian body.

6. The computer-implemented method of claim 1, wherein the interface is configured to facilitate interactions between the subject and a health coach responsible for monitoring the glycemic health state of the subject.

7. The computer-implemented method of claim 1, wherein the interface is configured to serve as an informative dashboard for the subject.

8. A non-transitory computer-readable medium with instructions stored thereon that, when executed by a processor, cause the processor to perform operations comprising:
 acquiring multiple explicit data values generated by a glucose monitoring device that monitors a blood glucose level of a subject,
  wherein the multiple explicit data values correspond to multiple time points;
 providing a statistical model based on the multiple explicit data values and the multiple time points;
 imputing one or more data values for the blood glucose level of the subject during a future time interval by applying the statistical model to the multiple explicit data values;
 predicting a future glycemic health state of the subject by performing an analytic process on the one or more imputed data values;
 constructing a data series that includes the multiple explicit data values and the one or more imputed data values,
  wherein the data series is indicative of an approximation of continuous monitoring of the time-varying blood glucose level;
 storing the data series in a database record associated with a subject profile; and
 performing an action based on the future glycemic health state.

9. The non-transitory computer-readable medium of claim 8, wherein the statistical model is a Gaussian process model comprising:
 a radial basis kernel designed to indicate that the blood glucose level is more likely to vary over longer time intervals than shorter time intervals; and
 a periodic kernel designed to ensure the one or more imputed data values conform with a periodic pattern of past explicit data values generated by the glucose monitoring device.

10. The non-transitory computer-readable medium of claim 8, wherein the statistical model is a Kalman filtering model configured to:
 for each imputed data value of the one or more imputed data values,
  produce an estimated value indicative of a predicted blood glucose level at a future time point;
  generate a variance measure indicative of uncertainty of the estimated value; and
  periodically update the estimated value using a state transition model.

11. The non-transitory computer-readable medium of claim 8, wherein the multiple explicit data values are generated by a blood glucose meter, a continuous glucose monitor, or any combination thereof.

12. The non-transitory computer-readable medium of claim 8, wherein the operations further comprise:
 posting a visualization of the data series as a glucose trace over time to an interface generated by a computer program executing on a computing device associated with an individual,
  wherein the visualization includes an error bar indicative of a confidence interval that overlays the glucose trace.

13. The non-transitory computer-readable medium of claim 8, wherein the operations further comprise:
 acquiring an additional explicit data value generated by the glucose monitoring device;
 comparing the additional explicit data value to a corresponding imputed data value in the data series;
 determining an accuracy measure for the statistical model based on said comparing; and
 altering the statistical model responsive to a determination that the accuracy measure falls below a threshold.

14. The non-transitory computer-readable medium of claim 8, further comprising:
 imputing one or more other data values for the blood glucose level of the subject during a past time interval by applying the statistical model to the multiple explicit data values,
  wherein at least one of the one or more other data values resides between the multiple explicit data values; and
 predicting a past glycemic health state of the subject by performing an analytic process on the one or more other imputed data values.

15. The non-transitory computer-readable medium of claim 8, wherein said performing comprises:
 causing display of a notification for review by the subject,
  wherein the notification includes a recommendation for improving the future glycemic health state.

16. An electronic device comprising:
 a memory that includes instructions for providing an imputation model configured to impute blood glucose measurements that are used to guide a subject toward a healthier glycemic health state,
 wherein the instructions, when executed by a processor, cause the processor to:
  acquire at least one explicit data value generated by a glucose monitoring device that monitors a blood glucose level of the subject;
  provide the imputation model based on the at least one explicit data value;
  impute at least one data value for the blood glucose level of the subject by applying the imputation model to the at least one explicit data value;
  predict a future glycemic health state of the subject by performing an analytic process on the at least one imputed data value;
  identify, based on the future glycemic health state, a recommendation regarding the generation of future explicit data values by the glucose monitoring device; and
  causing display of the recommendation on an interface generated by a computer program executing on a computing device associated with the subject.

17. The electronic device of claim 16, wherein the analytic process identifies a feature that is either reflected in the at least one explicit data value or derived from the at least one explicit data value or metadata provided with the at least one explicit data value.

18. The electronic device of claim 16, wherein the recommendation specifies a number of explicit data values that should be generated during a particular time interval, a time at which an explicit data value should be generated, or any combination thereof.

19. The electronic device of claim 16, wherein the instructions further cause the processor to:
- receive input indicative of an identification of a glucose-related metric,
  - wherein the recommendation is for the purpose of minimizing an error value associated with the glucose-related metric.

* * * * *